United States Patent [19]
Zhang et al.

[11] Patent Number: 5,563,068
[45] Date of Patent: Oct. 8, 1996

[54] BIOREACTOR

[75] Inventors: Shuyuan Zhang, Gaithersburg; Hitoshi Kotani, Middletown; Perry Newman, III, Odenton, all of Md.

[73] Assignee: Genetic Therapy, Inc., Gaithersburg, Md.

[21] Appl. No.: 230,627

[22] Filed: Apr. 21, 1994

[51] Int. Cl.$^6$ ................................................. C12M 3/00
[52] U.S. Cl. ............................ 435/295.2; 435/295.3; 435/299.1
[58] Field of Search ........................... 435/284, 285, 435/310, 313, 314, 295.1, 295.2, 295.3, 299.1

[56] References Cited

U.S. PATENT DOCUMENTS 5,057,428   10/1991   Mizutani et al. ..................... 435/285

FOREIGN PATENT DOCUMENTS 3818776   2/1988   Germany .

OTHER PUBLICATIONS

Looby, et al., Fixed bed porous glass sphere (porosphere) bioreactors for animal cells. Cytotechnology 1:339–346 (1988).

Chiou, et al., A fiber–bed bioreactor for anchorage–dependent animal cell cultures: Part I. Bioreactor Design and Operations. Biotechnology and Bioengineering 37:755–761 (1991).

*Primary Examiner*—David A. Redding
*Attorney, Agent, or Firm*—William Squire

[57] ABSTRACT

A stainless steel column housing is capped with an O-ring sealed cover to form a sealed autoclavable sterile chamber. A pair of stainless steel mesh circular cylindrical concentric inner and outer columns are within the chamber. A bed of porous glass spherical beads are packed in the region between the inner and outer mesh columns. The pH and DO are monitored and controlled while culture medium is continuously supplied to and from the sterile chamber. The outer mesh column forms an outer bulk medium chamber with the housing and the inner mesh column forms an inner bulk medium chamber. A ring sparger bubbles air and $CO_2$ mixture into the outer bulk medium chamber, the bubbles creating pressure differentials in the bulk medium chambers. These differentials cause radially bulk medium flow through the packed bead bed without pressure gradients in the bed and axial bulk medium recirculation flow in and between the inner and outer bulk medium chambers at their axial ends. The bioreactor is suitable for retroviral vector and animal cell culture production.

21 Claims, 6 Drawing Sheets

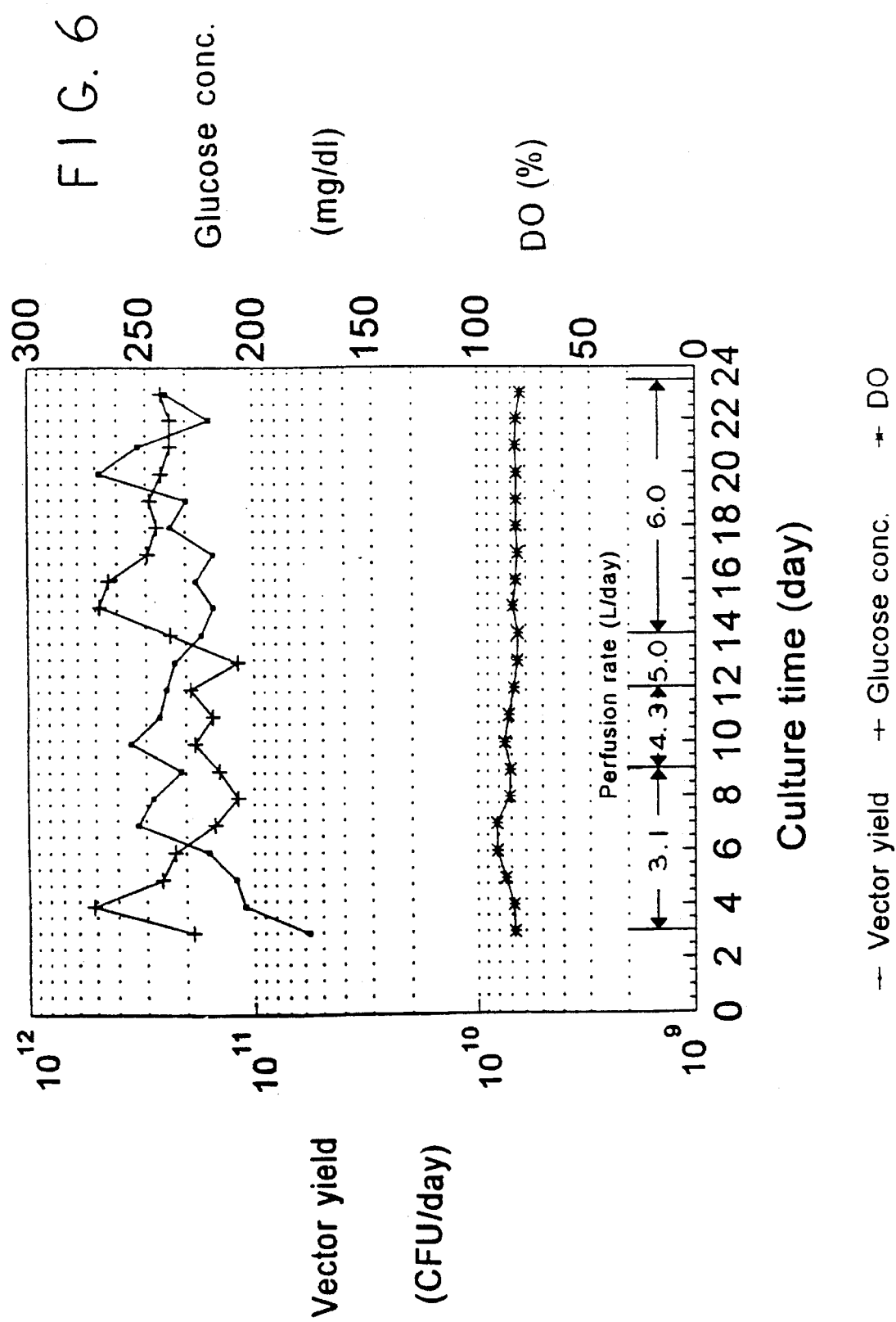

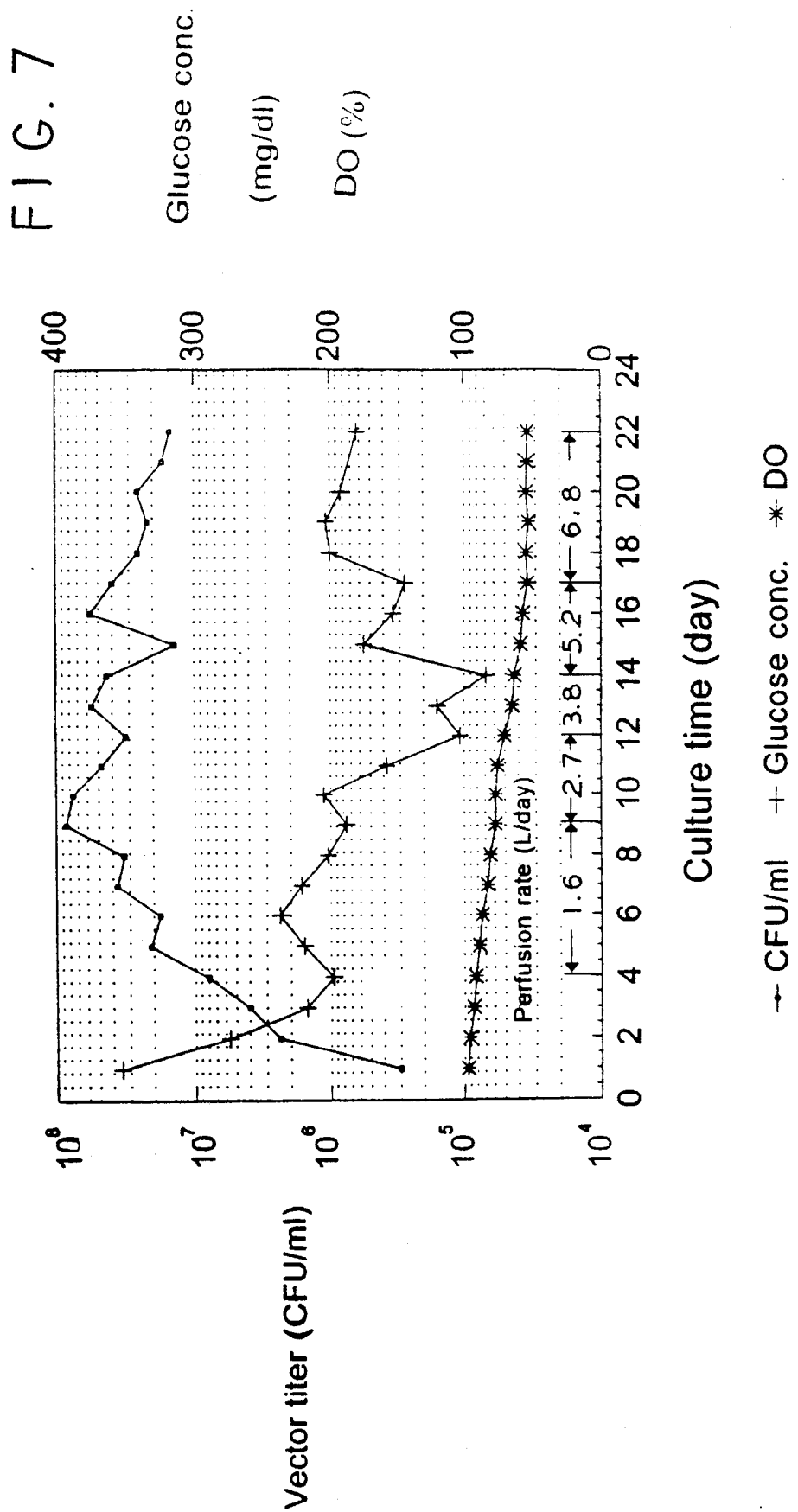

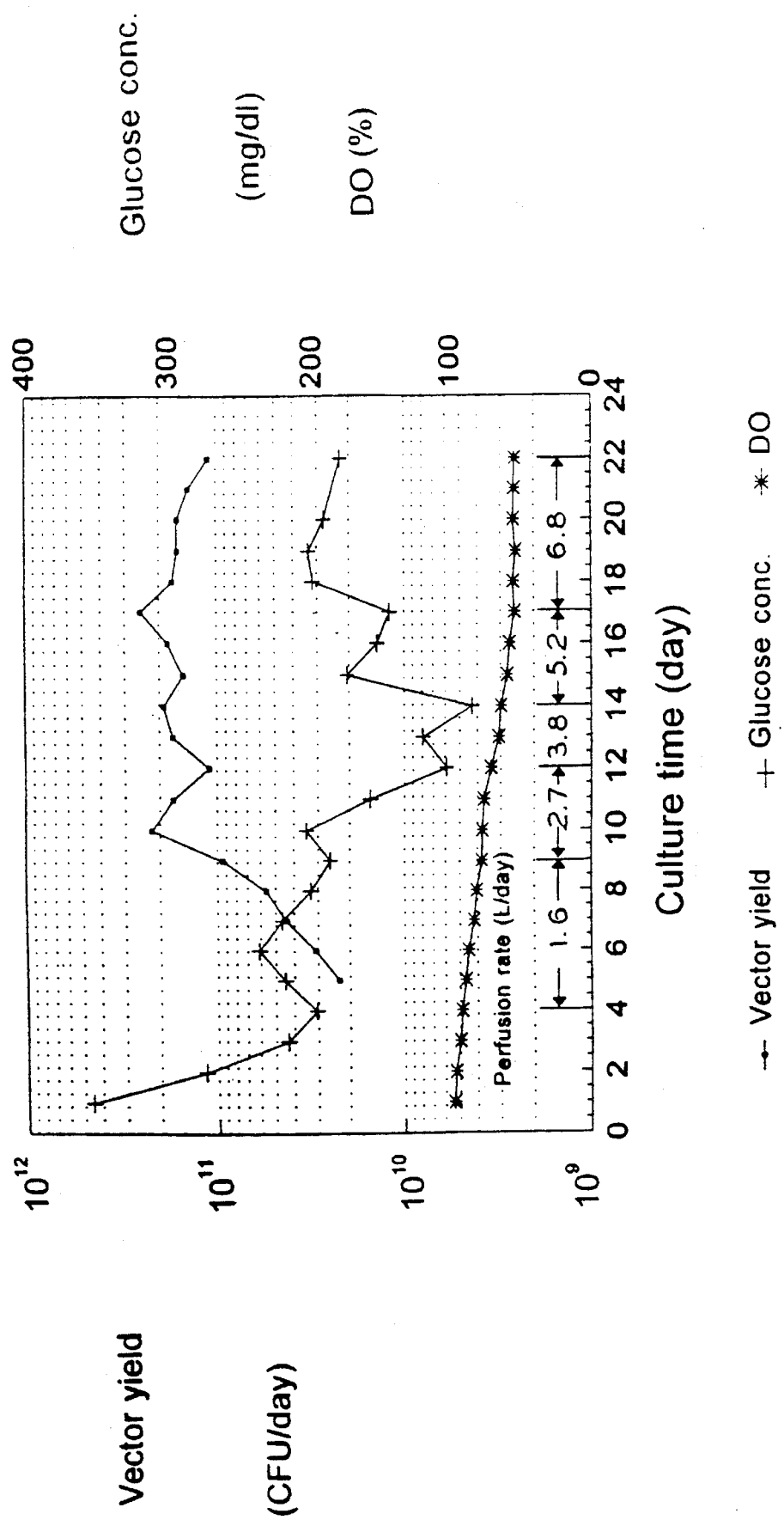

BIOREACTOR

BACKGROUND OF THE INVENTION

This invention relates to bioreactors, and more particularly, to fixed bed macroporous carrier culture high density generating systems.

Retroviral vectors are generally produced from producer cells grown in two-dimensional monolayer systems such as T-flasks, roller bottles, and other monolayer cell culture systems. Most of these systems have multiple processes for large-scale production. The number of cells is limited by the surface area of the culture system which limits the level of vector titer achievable with these systems. Also, extended stable vector production is difficult after cells reach 100% confluence in these systems, because of the possible detachment of cells from the culture surfaces.

Fixed bed porous glass sphere bioreactors for animal cells are known. For example, reference is made to an article *A fiber-Bed Bioreactor for Anchorage Dependent Animal Cell Cultures: Part I. Bioreactor Design and Operation* by Chiou et al., Biotechnology and Bioengineering, Vol. 37, Pp. 755–761 (1991). Disclosed is a bioreactor comprising an inner draft tube and an annular packed glass fiber bed. Cells are immobilized on the glass fibers in the annular region, and medium fills both the draft tube and the annular region. Air is introduced from the base of the tube and oxygenates the medium in the draft tube, and bubbles disengage at the upper fluid surface. The density difference between the aerated fluid in the draft tube and the bubble-free liquid in the annular fiber bed leads to global circulation of the medium in the bioreactor. The problem with this arrangement as recognized by the present inventors is one of efficient cell production and scale-up effectiveness. While the above article discloses high scale-up potential is expected, such scale-up is a function of the axial extent of the draft tube and annular region of glass fibers which is believed to be limited. Also, the medium flow through the fibers is only axial which is also believed to be limiting with respect to efficiency of culture production.

A second bioreactor system is disclosed in an article entitled *Fixed Bed Porous Sphere (Porosphere) Bioreactors for Animal Cells* by Looby et al., Cytotechnology 1: 339–346 (1988). Disclosed is a bioreactor in which solid glass spheres are replaced with open pore glass spheres. However, scale-up of the disclosed system is believed limited for reasons similar to those mentioned above in the Chiou article in that both systems disclose axial medium flow in the packed bed. Such prior art systems are limited in scale-up by the build up of pressure and nutrient gradients within the packed bead bed both axially and radially.

SUMMARY OF THE INVENTION

A bioreactor according to one embodiment of the present invention comprises a housing forming a cylindrical first chamber defining a longitudinal axis, first means for forming a cylindrical second chamber of a first given axial extent within and concentric with the first chamber, second means for forming a cylindrical third chamber of a second given axial extent within the first chamber concentric with and surrounding the second chamber and third means for forming a fourth chamber concentric with and surrounding the third chamber. The first, second and third means are arranged to permit fluid transfer between these chambers in a direction transverse the axis. A plurality of elements are provided in the third chamber for forming culture growing sites and are arranged to permit a culture growing medium fluid to flow therebetween. Means are included for delivering and removing the culture growing fluid medium into and from the first chamber. Gas means are provided for causing the medium to axially flow in the second and fourth chambers and flow transversely the axis between the second and fourth chambers through the third chamber and between the elements.

In a further embodiment, the first and second means each comprise a perforated annular sheet member and, preferably, the first and second means each comprise a sheet of wire mesh.

IN THE DRAWING

FIG. 6 is a graph showing the relationship between vector yield, glucose concentration and dissolved oxygen (DO) in the same example of FIG. 3 using a bioreactor of the embodiment of FIG. 1;

FIG. 7 is a graph showing the relationship between vector titer, glucose concentration and dissolved oxygen (DO) in Example 2 using a bioreactor of the embodiment of FIG. 1; and FIG. 8 is a graph showing the relationship between vector yield, glucose concentration 1 and dissolved oxygen (DO) in Example 2 using the bioreactor of FIG. 1.

DESCRIPTION OF THE PREFERRED EMBODIMENTS

Figure 1:
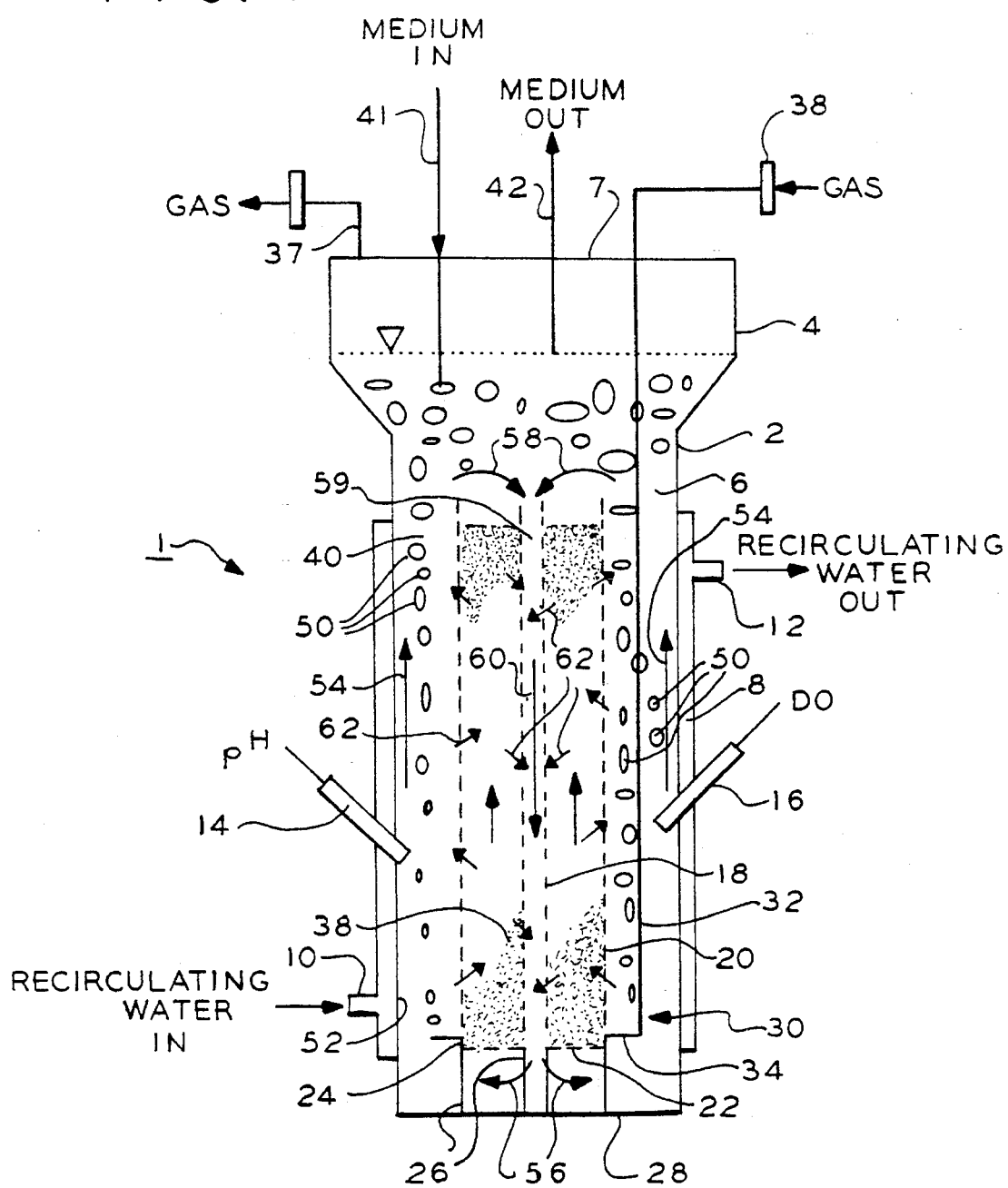
FIG. 1 is a diagrammatic sectional elevation view of a bioreactor according one embodiment of the present invention.

In FIG. 1, bioreactor 1 comprises a reactor column 2 which is preferably stainless steel but may be thermoplastic such as polypropylene. Column 2 forms a circular cylindrical housing with an enlarged mouth region 4 to allow for foaming within the column 2 during cultivation. Region 4 is optional. The column 2 has a removable cover 7 which is hermetically sealed to the column 2 over the mouth region 4. The cover is sealed with one or more O-rings (not shown) and latches or bolts (not shown). The column 2 with the cover is autoclaved to provide a sterile structure for culture growth. The column 2 is an integral structure with the various sections thereof welded or other wise sealed to form a moisture impervious sealed chamber 6.

A stainless steel water jacket 8 surrounds the column 2 for maintaining the interior of the column at the desired temperature, e.g., 37° C. Recirculating water is supplied at inlet 10 and exhausted at outlet 12. A pH probe 14 and a dissolved oxygen probe (DO) 16 are coupled to the column for measuring pH and DO of the culture medium in the column chamber 6. The probes are conventional.

Figure 3:
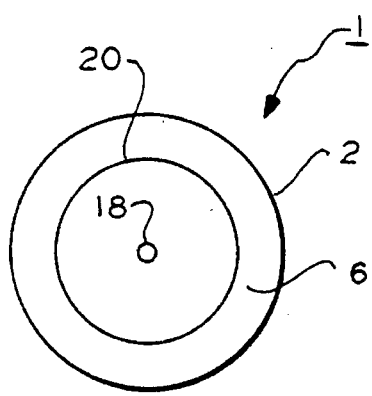
FIGS. 3 and 4 are respective diagrammatic plan sectional views of the bioreactor of FIG. 1 and a scaled-up bioreactor.

Located symmetrically within the chamber 6 are respective inner and outer elongated upstanding columns 18 and 20, FIGS. 1 and 3. The columns 18 and 20 are both circular concentric cylinders with the inner column 18 nested within the outer column 20. An annular flat ring washer-like bottom wall 22, FIG. 1, is secured between the inner and outer columns at the base region 24 thereof. The columns 18 and 20 and wall 22 are preferably made of the same material, e.g., stainless steel wire mesh. This mesh by way of example has a mesh gauge of 12 (12 openings per square inch) with a wire diameter of 0.016 inches. However, other perforated column structures and mesh or opening sizes may be used for the inner and outer columns in accordance with a given implementation. The present example is given for retroviral vector production. Other biological producer configurations may require different parameters.

Figure 4:
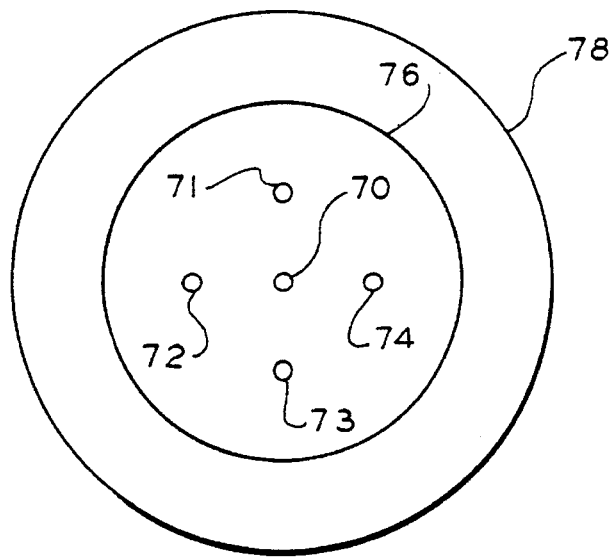

A plurality of upstanding legs 26 support the columns 18 and 20 and may comprise stainless steel rods welded to the bottom wall 28 of column 2. The column 2 and its structure as described herein is for a bench type unit, but for commercial vector production is scaled up in size, FIG. 4. For example, in a scale-up configuration, five inner columns 70–74 are employed in an outer column 76 within a reactor column 78. Each of the five inner columns 70–74, inclusive, are the same in diameter and material as column 18, FIG. 1. The diameter of the outer column 76 containing columns 70–74, however, is increased as compared to that of outer column 20, FIG. 1, as the diameter of the reactor column 2 increases during scale-up as illustrated by reactor column 78, FIG. 4. The lengths of the outer column 76 and reactor column 78 are also increased, as compared to the lengths of the outer and reactor columns 20 and 2, respectively, FIG. 1. The outer column and reactor column lengths are increased correspondingly as the diameters increase to maintain a length/diameter ratio of 5:1 of the outer column 76. The length of the inner columns 70–74 increases along with the length increase of the outer column 76. The multiple inner columns 70–74 are placed symmetrically within the outer column 76 as shown in FIG. 4 using five inner columns by way of example. These inner columns essentially form multiple chambers of packed bead beds in the region between and within the outer column 76. The radial distance between each of the inner columns 70–74 is maintained constant preferably at about 3–4 cm. This particular configuration maintains the scalability of the bioreactor of FIG. 1.

Figure 2:
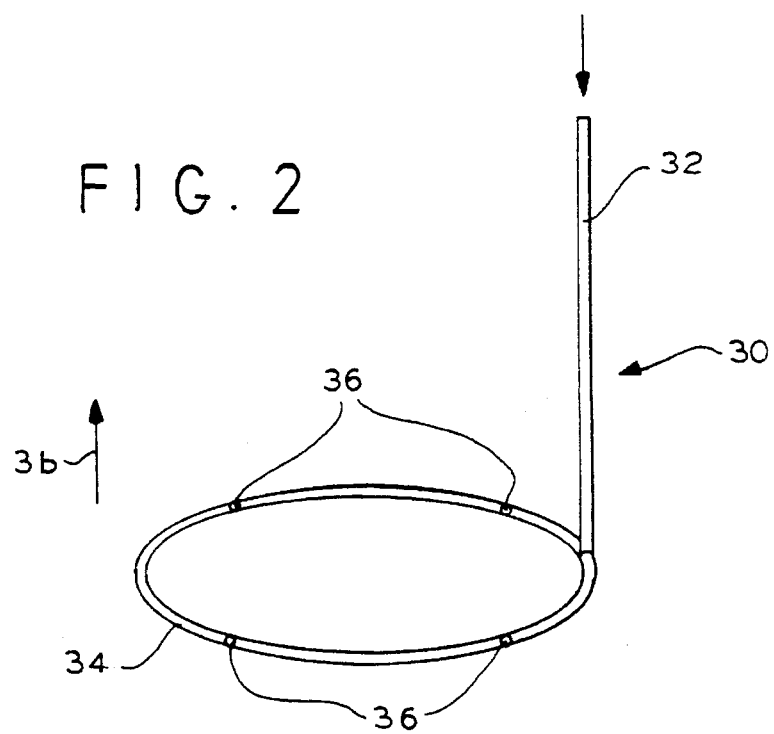
FIG. 2 is an isometric view of a sparger for use in the embodiment of FIG. 1.

A perforated ring sparger 30, FIG. 1, is in the chamber 6. In FIG. 2, the sparger 30 comprises an elongated gas inlet tube 32 coupled to a perforated tubular circular ring 34. In this embodiment the ring 34 has four orifices 36 of like dimensions, e.g., 0.5 mm, equally spaced about the ring 32. There may be more or fewer orifices in other embodiments according to a given implementation. The orifices face generally upwardly in direction 36 toward the cover 7 (FIG. 1). The sparger 30 is preferably stainless steel.

In FIG. 1, the tube 32 is welded to or otherwise attached sealed to cover 7 of column 2. The sparger 30 includes a gas inlet coupling 38 for receiving filtered pressurized gas, preferable air mixed with $CO^2$ (preferably 5% $CO^2$). The inlet and outlet gas is filtered with absolute 0.2 μm filters. The sparger and column 2 may be the same material. Gas flow rate is regulated by a flow meter (not shown) and is determined by the desired DO tension as measured by the probe 16 and an oxygen analyzer (not shown). The entire assembly is autoclaved to provide a sterile environment within the chamber 6. Preferably, the assembly is steam autoclaved. Gas is exhausted via exhaust tube 37.

Porous beads 38 are packed in the space between columns 18 and 20 forming a ring-like stack of beads supported by bottom wall 22. The beads are sintered porous glass spheres and preferably have a diameter range of about 3–5 mm, a pore size of 60–300 μm and a pore volume of 55–60%. The pores are sufficiently large to allow cells to migrate and grow in the interior of the bead. As a result, much higher cell concentration and subsequently higher vector titer can be achieved as compared to traditional monolayer culture systems. The beads are commercially available as Siran beads from Schott Process Systems, Vineland, N.J. The beads may also be gelatin and plastic material. The beads are retained by the inner and outer columns 18 and 20 and bottom wall 22. The beads may also be other shapes in accordance with a given implementation.

A culture growing medium 40, for example, Dulbecco's Modified Eagle's Medium (DMEM) +10% Foetal Bovine Serum (FBS) +0.1% Pluronic (non-ionic surfactant) +5 ppm antifoam agent. A specific medium is given by way of example in more detail in the example given below.

Medium from a medium bottle (not shown) kept at 4° C. is continuously delivered by a peristaltic pump (not shown) into the bioreactor via an autoclaved silicone inlet tube 41. The medium flow is continuous and the flow rate variable and regulated according to the glucose concentration inside the bioreactor chamber 6. The glucose concentration is maintained at ≧150 mg/dl by adjusting the medium perfusion rate. The medium input and output perfusion rate with respect to chamber 6 is important for optimized cell growth. Medium is continually harvested at the medium outlet tube 42 into a harvest bottle kept at 4° C. via a peristaltic pump (not shown). The pH in the medium is continuously monitored by probe 14 with the pH maintained at 7.0 to 7.3 by changing the percentage of $CO_2$ in the gas mixture. During a culture run, the medium is applied aseptically into and out of the bioreactor chamber 6 via the tubes 41 and 42, respectively.

By way of example, column 2 may have a diameter of 100 mm and a height of 500 mm. The ring 34 of the sparger 30 has a diameter of 80 mm with 4 mm sparger tubes and 0.5 mm orifices 36. The inner column 18 has a diameter of 8 mm and the outer column 20 has a diameter of 70 mm. The inner and outer columns have a height of 340 mm.

In operation, gas is applied to sparger 30 and the chamber 6 filled with flowing medium 40, the retroviral vector producer cells having been introduced to the packed bed of beads 38. The gas in the sparger flows out of orifices 36 creating bubbles 50. The bubbles 50 are created only in the annular ring chamber 52 between the outer column 20 and the housing column 2. The rising bubbles 50 create a low pressure beneath the bottom wall 22 as compared to the pressure at the top of the columns 18 and 20. This pressure differential causes the bulk medium 40 to axially flow upwardly in direction 54 in chamber 52. The medium flow at the bottom of the columns 18 and 20 is shown by arrows 56. The flow at the top of the columns 18 and 20 is in directions 58. The lower pressure at the bottom causes the medium to flow downwardly in the central chamber 59 formed by inner column 18 directions 60. As a result there is a gentle bulk medium recirculation in the chamber 6 outside the bed of beads 38.

The upward flow of medium in direction 54 and downward flow in direction 60 create various mild pressure differentials between the medium in the packed bead bed and the bulk medium in chambers 52 and 59. These pressure differentials cause a mild medium flow transversely through the bed of beads 38 represented by the smaller arrows in the directions 62. Thus, both axial flow in directions 54 and 60 and radial transverse flows in directions 62 are generated relative to the packed bed of beads 38. By optimizing the radial flow, the build up of undesirable pressure gradients within the packed bead bed can be effectively minimized.

The pressure differentials that are created are between the medium in the packed bead bed and the bulk medium flowing outside the bead bed. Since the bubbles are confined within the cell-free chambers 52 and 59, there is no direct bubble-cell interaction. The bubbles do not enter into the packed bead bed chamber. Thus, a relatively clearer supernatant which contains retroviral vectors can be produced for an extended time period.

Employing the bubbles to effect medium circulation, no external loop and movable mechanical parts are involved within the enclosed chamber 6. This renders the system completely enclosed with low risk of contamination and minimum maintenance required. This makes the system suitable for long term cultivation without interruption. The bioreactor as disclosed herein is appropriate for retroviral vector production and is superior to prior bioreactors.

Because of both the axial and radial medium flows of the present bioreactor, scale-up of this bioreactor is more feasible than in prior art systems comprising solely axial medium flow. Scale-up can be obtained by using multiple inner mesh columns within the outer column providing increased production efficiency.

While the bioreactor of the present invention has been disclosed for retroviral vector production, it can also be utilized for the production of secretable proteins, monoclonal antibodies and so on from cultured animal cells. Therefore, this bioreactor has a wider application in the large-scale animal cell culture field than prior systems.

EXAMPLE 1

Materials and Methods

Cell culture

Retroviral vector producer cell line PA317/G1TK1SvNa.7 was maintained routinely in T-flasks (Costar Corp. Cambridge, Mass. 02140) in Dulbecco's Modified Eagle's Medium (DMEM) with 4.5 g/l glucose (BioWhittaker, Walkersville, Md. 21793) supplemented with 10% Foetal Bovine Serum (FBS, Hyclone, Logan, Utah). Cells were cultured in an incubator at 37° C. with an atmosphere of 5% $CO_2$, 95% humidity. Cells were expanded into roller bottles (Corning, Corning, N.Y.) at an inoculation density of $1\times10'$ cells/$cm^2$ when required.

Culture medium for bioreactor

DMEM +10% FBS +0.1% Pluronic F-68 (Sigma, St. Louis, Mo.) +5 ppm antifoam C (Sigma) was used as the culture medium for the bioreactor.

Preparation of bioreactor 700 ml of porous Siran beads were packed into the bioreactor, which has a working volume of 1,600 ml. The beads in the bioreactor were washed once with deionized water before autoclave. The bioreactor was autoclaved at 120° C. for 45 min. After autoclave, the bioreactor was washed once with sterile Hank's Balanced Salt Solution (HBSS, BioWhittaker, Walkersville, Md. 21793). Then the bioreactor was filled with DMEM +10% FBS medium and left overnight to condition the porous beads for cell culture. Before cell inoculation, the bioreactor was washed once again with fresh DMEM +10% FBS.

Inoculation

Cells grown in roller bottles at a cell confluence of approximately 95% were trypsinized with trypsin/versene solution (Biowhittaker, Walkersville, Md. 21793). The trypsinized cells were washed once with DMEM +10% FBS and spun down at 1,500 rpm for 6 min in a centrifuge (Beckman GS-6KR) to remove residual trypsin. Resultant cell pellets were resuspended in culture medium. A total of $1\times10'$ cells suspended in 1,500 ml of culture medium were inoculated into the bioreactor. Immediately after inoculation, gas (5% $CO_2$ in air) sparging at a rate of 200 ml/min was started to ensure uniform cell distribution within the packed bed.

Sampling

Daily sample of 4 ml was taken from the bioreactor aseptically. The sample was filtered through a 1.2 μm filter to remove any cells and cellular debris. Glucose concentration of the sample was measured using a glucose analyzer (Accu-Check® IIm, Boehringer Mannheim). The remaining sample was frozen at −70° C. for future viral vector titer assay.

Perfusion in bioreactor

Medium perfusion was started when the glucose concentration dropped to 150 mg/dl in the bioreactor. Perfusion rate was regulated by a peristaltic pump (Masterflex, Cole-Parmer, Chicago) according the glucose concentration which was maintained at ≧150 mg/dl in the bioreactor. Gas sparging rate was controlled by a gas flow meter according to the dissolved oxygen (DO) tension which was maintained at ≧80% of air saturation in the bioreactor. Culture temperature was maintained at 37° C. unless otherwise stated.

Titer assay

Amphotropic retroviral vector produced by PA317/G1TK1SvNa.7 producer cells, which carries the neomycin-resistant selective marker, was assayed by a G418 selection method using NIH 3T3 TK-cells as target cells. On day one, NIH 3T3 TK- cells were seeded at $1\times10'$ cells/well of a 6-well tissue culture plate (Becton Dickinson, Lincoln Park, N.J.) and incubated at 37° C. in 5% $CO_2$. On day two, serial ten-fold dilutions of samples taken from the bioreactor in medium containing 8 μg/ml polybrene was added to the target cells and incubated at 32° C. for an additional 24 h. On day three, the medium was aspirated and replaced with medium containing 800 μg/ml G418. Plates were incubated at 37° C. in 5% $CO_2$. On day six, plates were refed with medium containing 800 μg/ml G418. On day eight, colonies were stained with methylene blue and the vector titer was calculated as the number of colony forming units (CFU) per ml.

Results

Figure 5:
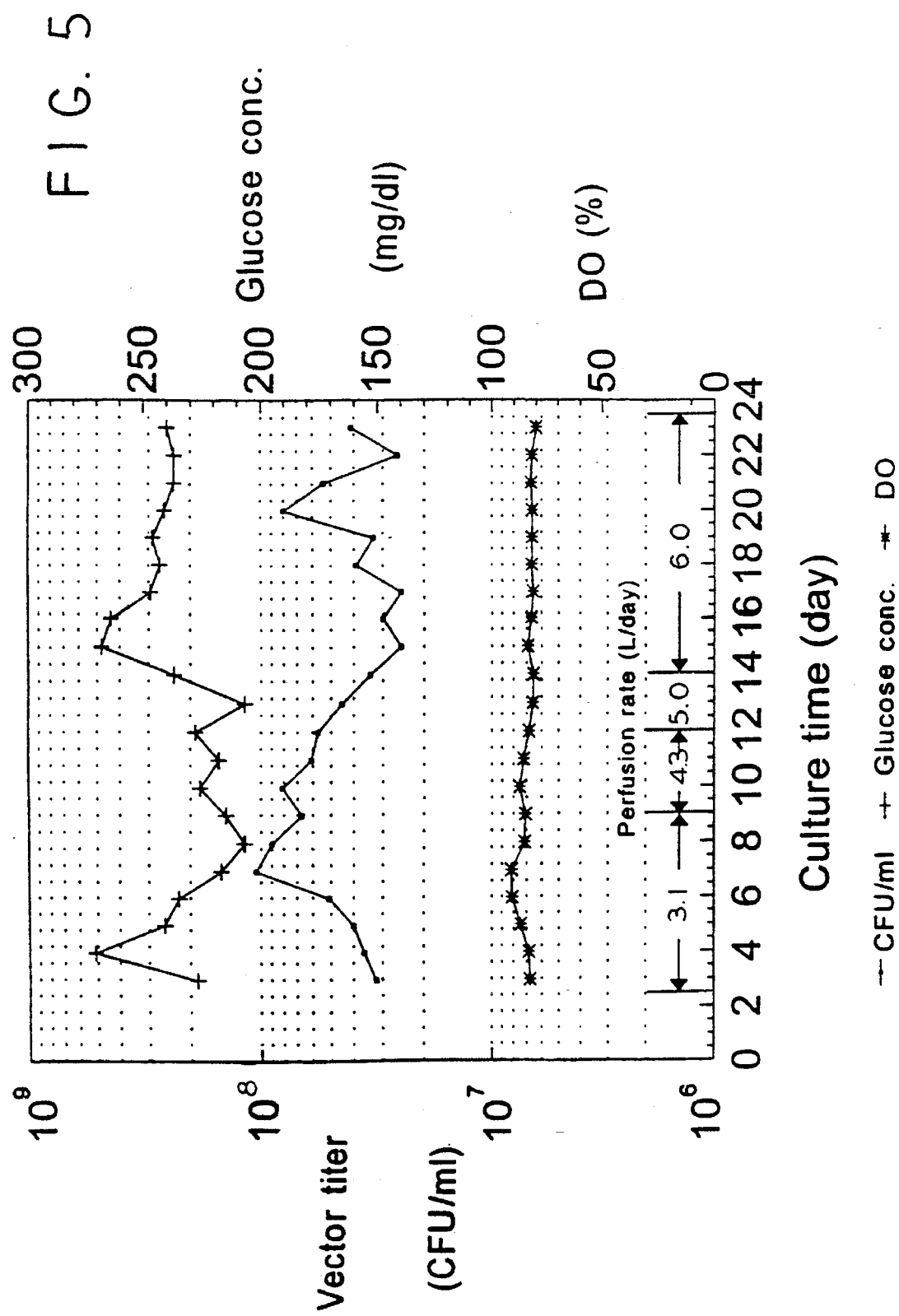
FIG. 5 is a graph showing the relationship between vector titer, glucose concentration and dissolved oxygen (DO) in example 1 using a bioreactor of the embodiment of FIG. 1.

PA317/G1TK1SvNa.7 retroviral vector producer cells were cultured in the bioreactor for 23 days with continuous medium feeding and harvesting. FIG. 5 shows the viral vector titer in relation to glucose concentration and DO tension. An averaged vector titer of $5\times10^7$ was maintained. Vector titer as high as $1\times10^8$ CFU/ml was achieved, which is 7–5 fold higher than the titer achieved in roller bottle cultures ($1$–$2\times10^7$ CFU/ml). Since the culture was conducted with continuous medium feeding and harvesting, vector yield, which is a function of the perfusion rate and the vector titer, is a more appropriate parameter to evaluate the performance of the bioreactor. FIG. 6 shows the relationship of daily vector yield glucose concentration and DO tension in the bioreactor. The numbers in the graph indicate daily perfusion rate. Vector yield increased steadily in the early stage of the culture when exponential cell growth is expected. As the culture progressed further, vector yield remained relatively constant at a value of $1.5\times10^{11}$ CFU/day. The stabilization of vector yield is likely to be the result of producer cells reaching a stationary phase inside the bioreactor. The relatively short exponential growth phase observed in this culture is related to the large number of cells inoculated into the bioreactor ($1\times10^9$ cells). Replication competent retroviral (RCR) vector assay at the end of the culture was negative.

EXAMPLE 2

To examine the effect of inoculation cell number on the production of retroviral vector from the bioreactor of FIG. 1, an experiment was conducted in the bioreactor using a less number of inoculation cells of $2 \times 10^8$ instead of $1 \times 10^9$ producer cells as inoculated in Example 1. Except for the difference in inoculation cell number, the same operation conditions were used in this experiment as for Example 1.

The culture was run for 22 days with continuous medium feeding and harvesting. FIG. 7 shows the viral vector titer in relation to glucose concentration and DO tension. Vector titer increased gradually from $2 \times 10^5$ CFU/ml on day one to $8.5 \times 10^7$ CFU/ml on day nine, which represents an increase in vector titer of more than 2 logs. This is in contrast to the relatively small increase in vector titer in the early stage observed in Example 1, where it was attributed to the large inoculation cell number of $1 \times 10^9$ producer cells. This suggests that a prolonged exponential growth phase was maintained in the bioreactor with a low inoculation cell number. An averaged vector titer of $3.1 \times 10^7$ CFU/ml was maintained with a titer as high as $8.5 \times 10^7$ CFU/ml achieved. FIG. 8 shows the relationship of daily vector yield, glucose concentration and DO tension in the bioreactor. Vector yield increased rapidly in the early stage of the culture. As the culture progressed further, vector yield levelled off and then remained relatively stable at a value of $1.5 \times 10^{11}$ CFU/day. This result is in accordance with the result reported in Example 1. Replication competent retrovirus (RCR) assay at the end of the culture was negative.

It should be understood that various modifications of the embodiments described herein may be made by one of ordinary skill and that the disclosed embodiments are given by way of example and not limitation. The scope of the present invention is as defined in the appended claims.

What is claimed is:

1. A bioreactor comprising:
   a housing forming a cylindrical first chamber defining a longitudinal axis, said chamber having an upper and a lower end;
   first means for forming a cylindrical second chamber of a first given axial extent between said upper and lower ends within the first chamber;
   second means for forming a cylindrical third chamber of a second given axial extent within the first chamber and surrounding the second chamber;
   said housing and second means forming a fourth chamber surrounding the third chamber, the first and second means being arranged to permit fluid transfer between the second and fourth chambers in a direction transverse the axis;
   a plurality of elements in said third chamber for forming a fixed bed of a plurality of culture growing sites and arranged to permit a culture growing medium fluid to flow therebetween;
   means for delivering and removing said culture growing fluid medium into and from said first chamber; and
   gas means including a plurality of spaced apertures adjacent to said lower end in said first chamber for creating oxygen containing bubbles in said first chamber at said lower end, said bubbles, in response to buoyant forces thereon by said medium fluid, rising in said fluid for causing said medium to axially flow in said second and fourth chambers and flow transversely said axis between the second and fourth chambers through the third chamber and between said elements.

2. The bioreactor of claim 1 wherein the first and second means each comprise a perforated annular sheet member.

3. The bioreactor of claim 1 wherein the first and second means each comprise a sheet of wire mesh.

4. The bioreactor of claim 1 wherein the housing has a bottom wall, said gas means comprising an annular tube with a plurality of spaced orifices adjacent to and spaced from the bottom wall aligned with said fourth chamber.

5. The bioreactor of claim 1 wherein the elements are porous beads.

6. The bioreactor of claim 1 wherein the first chamber has upper and lower regions relative to the force of gravity, said gas bubbles being positioned in the first chamber to rise relative to the force of gravity in said fourth chamber creating a pressure drop in said lower region such that said medium flows toward said lower region through said second chamber from said upper region.

7. The bioreactor of claim 6 wherein the apertures and gas bubbles are arranged so that the flowing medium exhibits pressure gradients between said second and fourth chambers for causing said transverse flow.

8. The bioreactor of claim 1 wherein the culture comprises retroviral vectors.

9. The bioreactor of claim 1 wherein the culture comprises animal cells.

10. The bioreactor of claim 1 wherein the second, third and fourth chambers are concentric.

11. The bioreactor of claim 1 wherein the first and second means comprise cylindrical columns with perforations, the perforations being dimensioned smaller than said elements to retain said elements within said third chamber and arranged to preclude said bubbles from entering said third chamber.

12. The bioreactor of claim 1 wherein the second and third chambers terminate at said upper and lower ends, said medium being caused to flow radially in the first chamber from the second chamber to the fourth chamber at said lower end and radially from the fourth chamber to the second chamber at said upper end.

13. The bioreactor of claim 1 wherein the third chamber has a transverse radial thickness normal to said axis of about 3–4 cm.

14. The bioreactor of claim 1 wherein the first and second means comprise concentric spaced circular cylindrical wire mesh of about the same gauge openings and the same gauge wire, said third chamber having a bottom wall comprising said wire mesh for supporting said elements.

15. The bioreactor of claim 14 wherein the elements form a bed in said third chamber having a height to transverse radial width ratio of about 5:1–6:1.

16. The bioreactor of claim 1 wherein the medium and the gas bubbles are arranged so that the flowing medium has a mixing time in said first chamber of about 5–10 seconds.

17. A bioreactor comprising:
   a housing including a bottom wall, a top wall and a cylindrical side wall forming a cylindrical sealable sterile first chamber for growing culture therein and defining a longitudinal axis;
   an inner perforated cylindrical member in and concentric with said chamber forming a cylindrical second chamber;
   an outer perforated cylindrical member in said first chamber coextensive with, concentric with and surrounding said inner member forming an annular third chamber with said inner member extending along said axis;
   said housing for forming an annular fourth chamber with said outer perforated cylindrical member;

a perforated wall connected to and between the inner and outer members adjacent to and spaced from said housing bottom wall forming a bottom wall of said third chamber;

a plurality of elements in said third chamber supported on said perforated annular bottom wall for forming a fixed bed of culture growing sites;

means for delivering and removing a culture growing flui medium into and from said first chamber; and a plurality of spaced apertures for creating oxygen carrying gas bubbles in said medium so that the bubbles in response to the force of gravity on said medium rise in said medium in said annular fourth chamber and cause said medium to axially flow in said second and fourth chambers and transversely flow between the second and fourth chambers through the third chamber.

18. The bioreactor of claim 17 wherein the inner and outer cylindrical members and annular bottom wall are wire mesh.

19. The bioreactor of claim 17 wherein the elements comprise porous beads packed in said third chamber and arranged so that the fluid medium flows therebetween in said transverse flow.

20. The bioreactor of claim 19 wherein the beads have a diameter of about 3–5 mm and the inner and outer cylindrical members are 12 gauge wire mesh.

21. The bioreactor of claim 18 wherein the radial transverse thickness of said third chamber between the second and fourth chambers is about 3–4 cm.

* * * * *

UNITED STATES PATENT AND TRADEMARK OFFICE
CERTIFICATE OF CORRECTION

PATENT NO.  : 5,563,068
DATED       : October 8, 1996
INVENTOR(S) : Zhang, et al.

It is certified that error appears in the above-indentified patent and that said Letters Patent is hereby corrected as shown below:

- Title Page "[75] Inventors":

Change "Perry Newman, III" to read -- Perry B. Newton, III --.

Signed and Sealed this

Thirteenth Day of May, 1997

Attest:

BRUCE LEHMAN

Attesting Officer     Commissioner of Patents and Trademarks